Figure 1:
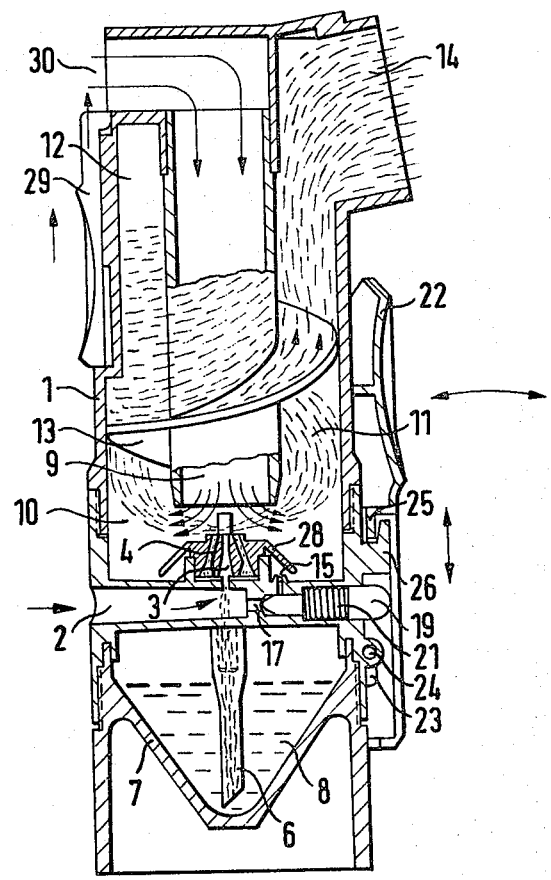

United States Patent [19]

Brugger et al.

[11] 4,429,835
[45] Feb. 7, 1984

[54] SPRAY-DIFFUSER

[75] Inventors: Inge Brugger, Prinz Karl Str. 50a, D-8130 Starnberg; Emeram Steil, Starnberg, both of Fed. Rep. of Germany

[73] Assignee: Inge Brugger, Starnberg, Fed. Rep. of Germany

[21] Appl. No.: 321,013

[22] Filed: Nov. 13, 1981

[30] Foreign Application Priority Data

Nov. 17, 1980 [DE] Fed. Rep. of Germany ....... 3043377

[51] Int. Cl.$^3$ ...................... B05B 7/00; A61M 11/02; A61M 15/00
[52] U.S. Cl. ............................... 239/338; 128/200.18; 222/637; 239/370
[58] Field of Search ............................ 239/338, 370; 128/200.14, 200.18, 200.19, 200.21; 261/DIG. 65; 222/630, 637, 635

[56] References Cited

U.S. PATENT DOCUMENTS 3,658,059  4/1972  Steil ................................ 128/200.12

FOREIGN PATENT DOCUMENTS 464801  7/1951  Italy ................................ 128/200.21
518220  7/1976  U.S.S.R. ......................... 128/200.21

Primary Examiner—Andres Kashnikow
Attorney, Agent, or Firm—Sughrue, Mion, Zinn, Macpeak and Seas

[57]  ABSTRACT

The invention relates to a spray-diffuser for the atomization of liquids or solid substances, such as medicaments, with the help for the flow of compressed air, particularly for inhalation purposes. The spray-diffuser comprises a spray-diffuser nozzle (3) located in an atomizing chamber (10), which nozzle is connected to a compressed air channel (2) and comprises a suction device for sucking up the medicament, wherein the compressed air channel adjacent the nozzle has a release opening (15) for escape of the compressed air, which opening is settable to a non-operation position, and which can for example be closed during inhalation of the patient and opened during exhalation of the patient. In known spray-diffusers, diverted air is guided through the release opening with a development of a hissing noise and a danger of harm to the staff. In order to avoid this disadvantage, in the spray-diffuser according to the invention the release opening leads into the atomizing chamber. Expediently, the release opening is positioned on that side of the compressed air channel which is averted from the supply chambers 7 for the substance to be atomized.

15 Claims, 3 Drawing Figures

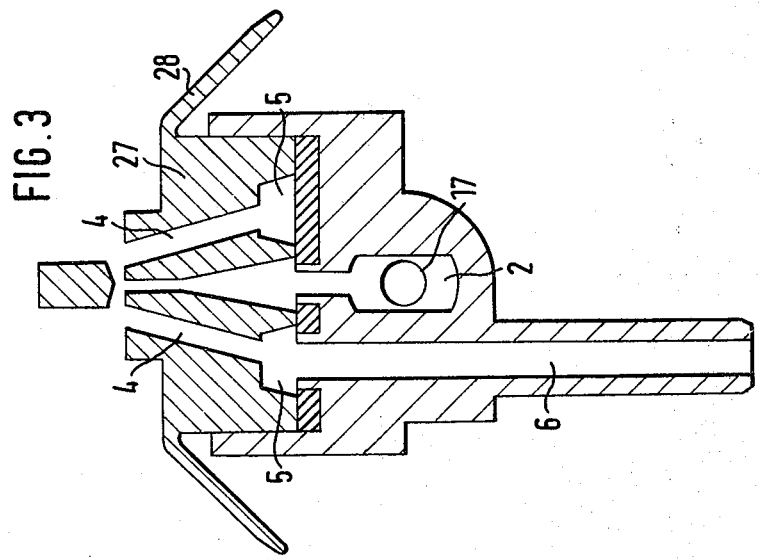
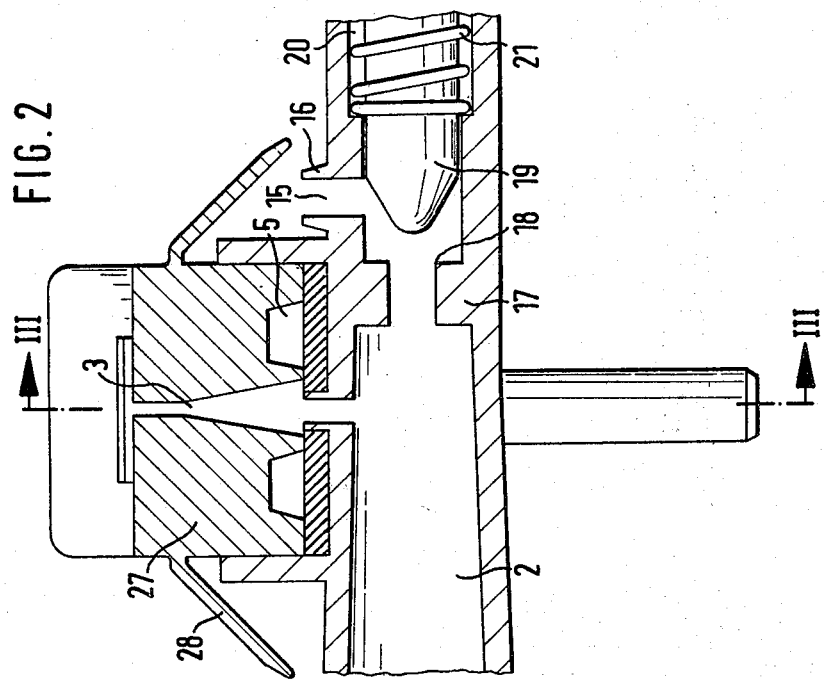

SPRAY-DIFFUSER

The invention relates to a spray-diffuser for the atomisation of liquids or solid substances, such as medicaments, with the help of a flow of compressed air, especially for inhalation purposes, having a spray-diffuser nozzle situated in an atomizing chamber, which nozzle is connected to a compressed air channel, and having a suction arrangement for sucking the medicament, wherein the compressed air channel adjacent the nozzle, has for escape of the compressed air a release opening which is settable to a non-operating position. With known spray-diffusers of the above-described type the substance to be atomized is conveyed, after atomisation in sucked-in air, with the air to an outlet of the spray-diffuser housing, in order, for example with inhalation apparatus, to be inhaled by the patient. Since atomized medicament must only be supplied to the patient during his inhalation period, atomisation can become intermittent with known spray-diffusers. To this end, the compressed air channel is provided near by with a release opening serving for escape of the pressurized air and is settable, e.g. closable, for other functions, which release opening can be closed during inhalation and opened during exhalation. When the release opening is open, compressed air arriving in the compressed air channel flows out through the release opening, without being forced away through the nozzle. Atomisation thus does not take place.

With the known spray-diffuser, the compressed air conducted into the open through this release opening leads to an audible irritating intermittent noise and allows an external air stream to result. This produces the risk that this air stream flows onto the hand or into the eyes of the inhaling patient, which can be very unpleasant for him.

The invention has the underlying object of overcoming the above mentioned disadvantage of the spray device of the introductory type. This is achieved in a suitable inventive manner, in that the release opening leads into the atomising chamber. By this means, audible intermittent air noise external of the spray device as well as the pleasant occurence of air streams flowing to the outside of the spray device housing are avoided. Furthermore, with application of the apparatus for inhalation purposes, by this means is achieved the not inconsiderable advantage that also, during exhalation, at the open release opening a somewhat higher air pressure remains in the atomising chamber, which air pressure hinders entry of exhaled air into the atomising chamber during exhalation of the patient, in order to prevent the patient inhaling it again, which would bring about an undesirable reduction in the fresh air content of the next breath.

In a preferred embodiment the release opening lies on that side of the pressurized air channel which is averted from the receiving chamber for the substance to be atomized. By this means is prevented uncontrolled eddying of the substance during release of the compressed air. Thus, the reception chamber for the substance to be atomized is as a rule positioned beneath the pressurized air channel and its spray-diffuser nozzle, should the outlet opening with the above positioned nozzel likewise be positioned towards the top of the atomising chamber in the operation conditions of the spray-diffuser. The outlet opening suitably has a column-like collar situated on the outside of the compressed air channel, which collar prevents entry of crude or not yet atomized substance. In addition, this collar can serve to guide escaping air to a return bottle which can be positioned over the release opening in the atomising chamber.

In a preferred form of the spray-diffuser according to the invention, the release opening is arranged in a part of the compressed air channel which part leads near the spray-diffuser nozzle and is closable between the nozzle and the release opening by means of a hand-operable valve having a valve member which is movable inwards in the direction of the axis of the channel part therein.

Further particulars and advantages of the invention will be found from the particularly preferred embodiment of the spray-diffuser which is illustrated in the drawing which will be described in more detail in the following:

FIG. 1 shows a vertical section through this preferred embodiment;

FIG. 2 illustrates a vertical section through the compressed air channel in the region of the spray-diffuser nozzle and the release opening on a larger scale;

FIG. 3 is a vertical section through the spray-diffuser nozzle and compressed air channel along line III of FIG. 2.

The drawing represents inhalation apparatus forming a practical realisation of the suitably inventive spray-diffuser which in the lower part of the cylindrical spray-diffuser housing 1 is provided with a closable compressed air channel 2 for connection to a source of compressed air. The channel 2 extends from the periphery of the spray-diffuser housing 1 towards the inside of the housing to the axis of the housing and beyond. In the region of the housing axis the spray-diffuser nozzle 3 is connected to the compressed air channel, which spray-diffuser nozzle 3 has an intake channel 4 leading into an annular channel 5, through which intake channel 4 the substance (medicament) which is to be atomized can be conveyed to the nozzle outlet, which extends via a suction pipe 6 from an intake chamber 7 for the medicament 8 which is to be atomized, which chamber 7 is situated below the compressed air channel 2.

Above the nozzle is provided a tubular intake channel 9 which is arranged coaxially in the spray-diffuser housing 1 and at a small distance above the nozzle. The underpressure caused at the upper side of the nozzle by the atomising process sucks in additional air through this intake channel. This additional air with the emergent compressed air from the nozzle and the atomized medicament mix in the atomisation chamber 10 form a homogenous cloud 11, which cloud flows in between the spray-diffuser housing 1 and the intake channel 9 which together form an annular channel 12 along a helical flank 13 to the outlet 14 in order there, directly or via a mouth piece connected thereon, to be inhaled by the patient.

The end of the compressed air channel 2 within the spray-diffuser housing 1 extends to a release opening 15 facing upwards within the atomising chamber 10, which release opening 15 is provided at the outside of the compressed air channel 2 with a supportive collar 16. The compressed air channel 2 is provided between the release opening and the spray-diffuser nozzle with a steplike constriction 17, which forms a stop surface, for example the seat 18, for a valve member 19, which is slidable inwards in the direction of the channel axis from the withdrawn position in compressed air channel 2 shown in FIG. 2 in which position release opening 15 is open up to the stop on the valve seat surface (FIG. 1) in which position of the valve member the release opening 15 closes. For this purpose, the valve member is mounted for longitudinal sliding in a bore 20 forming an extrusion of compressed air channel 2 in the spray-diffuser housing 1, in which bore is arranged a pressure spring 21 which seeks to urge the valve member to the withdrawn position shown in FIG. 2.

The outer end of the valve member projects from the spray-diffuser housing 1. Against this projection end lies an operating slide 22 which is mounted with a slot 23 on a king-pin 24 secured to the spray-diffuser housing 1. When the operating slide is moved by the patient to the lower position illustrated in FIG. 1, it slides, having regard to the arrangement of the valve member 19, to a position which in the case of FIG. 1 is an inner position, in which the valve member closes the release opening 15 and the constriction of the compressed air channel 2. In this position of the valve member no compressed air can flow through the release opening 15, so that necessarily emerging from the nozzle 3 in the atomising chamber 10 of the spray-diffuser will be medicament sucked up from the medicament chamber 7 via the suction pipe 6 and atomized in air drawn simultaneously into the atomising chamber 10 via the suction channel 9. When the operating slide is released, valve member 19 can move by means of the pressure spring 21 to the position illustrated in FIG. 2, in which position it opens the release opening 15 through which then compressed air from the compressed air channel 2 escapes. As a result, compressed air no longer flows from the nozzle 3 so that in this position of the valve no atomisation takes place.

In order to be able to hold the valve member in the inner position illustrated in FIG. 1 in which it closes the release opening 15 there is provided on the under side of the operation slide facing towards the spray-diffuser housing 1, a stop lug 25 which, through sliding of the opening slide by its slot 23 on the king pin 24 to the lower position illustrated in FIG. 1, is able to move behind a catch operating as a stop 26 on the outside of the spray-diffuser housing 1, thus holding the operating slide in the lower position.

Circumferentially of the cylindrical body 27 of the nozzle 3 is provided a roof-like integral shield 28 which extends over the release opening 15 and causes deflection of the compressed air flowing from the release opening. As a result, dispersion of the air is produced in order to achieve a reduction in the noise originating from release of the compressed air inside the spray-diffuser.

For alteration of the input of additional air, in the upper region of the spray diffuser on the outside of the housing a dose-setting slide 29 is mounted for up and down movement so that it can slide over the entrance opening 30 of the suction channel 9 to any position up to full uncovering of the opening. By this means the input amount of additional air can be regulated in order to be able to adjust the amount and density of the cloud flowing from the spray-diffuser via the discharge outlet 14.

We claim:

1. A spray-diffuser for the atomisation of liquids or solid substances, such as medicaments, with the help of a flow of compressed air especially for inhalation purposes, having located in an atomisation chamber a spray-diffuser nozzle which is connected to a compressed air channel and having a suction arrangement for sucking up the medicament, whereby the compressed air channel adjacent the nozzle has, for escape of the compressed air, a release opening which is settable to a non-operating position, characterized in that the release opening (15) leads into the atomisation chamber (10) in its operating position during exhalation and that the channel also has an atomizing opening leading to said nozzle for inhalation.

2. A spray-diffuser according to claim 1, characterized in that a supply chamber (7) for the substance to be atomized is mounted below the nozzle and that the release opening (15) lies on that side of the compressed air channel (2) which is averted from the supply chamber (7).

3. A spray-diffuser according to claim 1, characterized in that above the release opening (15) in the atomisation chamber (10) is provided a deflection surface for deflecting the compressed air escaping through said release opening.

4. A spray-diffuser according to claim 3, characterized in that the deflection surface is formed as a shield (28) on said nozzle near the release opening (15) and extends away over the release opening (15).

5. A spray-diffuser according to claim 4, characterized in that the shield (28) extends around the entire periphery of the nozzle.

6. A spray-diffuser according to any one of claims 1 to 5, characterized in that the release opening (15) has a collar (16) on the outside of the compressed air channel 2.

7. A spray-diffuser according to claim 1, characterized in that the release opening (15) is arranged in a part of the compressed air channel (2) which part leads past the spray-diffuser nozzle (3) and is capable of closing, by means of a hand-operable valve, communication between the nozzle and the release opening.

8. A spray-diffuser according to claim 7, characterized in that the valve has a valve member (19) which is movable inwards in the direction of the axis of that part of the channel located behind the nozzle 3.

9. A spray-diffuser according to claim 8, characterized in that the release opening is arranged in the side wall of that part of the channel located behind the nozzle (3), and the valve member (19) is slidable inwardly into this channel part beyond the release opening, in which inwardly slid position it closes the release opening.

10. A spray-diffuser according to claim 8, characterized in that the part of the channel located behind the nozzle (3) has a graded constriction of its inner dimensions between the nozzle and its release opening (15), which constriction serves as a valve seat (18) for the valve member.

11. A spray-diffuser according to claim 9, characterized in that the valve member (19) is urged back by a pressure spring (21) to a position in which the release opening (15) is open.

12. A spray-diffuser according to claim 9, characterized in that the end of the valve member (19) which is opposite from the end which is inwardly movable in the compressed air channel (2) projects from the spray-diffuser housing (1), and in that on this opposite end is provided an operating slide (22) which is slidably mounted on the outside of the spray-diffuser housing.

13. A spray-diffuser according to claim 12, characterized in that the operating slide (22) is arrestable on the spray-diffuser housing (1) in its depressed position, with the valve member (19) in its inwardly slid condition.

14. A spray-diffuser according to claim 13, characterized in that when the operating slide (22) is arrested in the inoperable position with the valve member (19) in its inwardly slid condition, a pin sits in a slot (23) on a rotation axis (24) secured to the spray-diffuser housing (1), and for the extent of the slot is movable on the axis, and in that a stop surface on the operating slide can be brought against a stop (26) on the spray-diffuser.

15. A spray-diffuser according to claim 12 characterized in that a suction channel (9) is mounted above the nozzle, and that a dose-setting slide means (29) is slidably mounted on the spray-diffuser for varying the size of the channel opening (30), thereby varying the amount of air sucked in through the channel (9).

* * * * *